United States Patent [19]

Meinard et al.

[11] Patent Number: 5,051,306
[45] Date of Patent: Sep. 24, 1991

[54] MICROENCAPSULATION PRODUCT AND PROCESS

[75] Inventors: Colette Meinard, Marseilles; Claude Taranta, Aix-en-Provence, both of France

[73] Assignee: Roussel Uclaf, Paris, France

[21] Appl. No.: 527,111

[22] Filed: May 21, 1990

[30] Foreign Application Priority Data

May 25, 1989 [FR] France ................. 89 06837

[51] Int. Cl.⁵ .............................................. B01J 13/16
[52] U.S. Cl. .............................. 428/402.21; 264/4.7; 428/402.22; 424/408; 424/462; 514/963
[58] Field of Search ............... 264/4.7; 428/402.21, 428/402.22; 424/408, 462; 514/963

[56] References Cited
U.S. PATENT DOCUMENTS

| 4,037,353 | 7/1977 | Hennart et al. | 43/129 |
| 4,046,741 | 9/1977 | Scher | 260/77.5 A |
| 4,376,113 | 3/1983 | Suglia et al. | 424/34 |
| 4,428,983 | 1/1984 | Nehen et al. | 427/213.34 |
| 4,675,249 | 6/1987 | Bowman | 428/402.1 |
| 4,722,838 | 2/1988 | Tocker | 424/81 |
| 4,738,898 | 4/1988 | Vivant | 428/402.21 |
| 4,876,290 | 10/1989 | Vivant | 521/76 |
| 4,956,129 | 9/1990 | Scher et al. | 264/4.7 |

Primary Examiner—Robert L. Stoll
Assistant Examiner—N. Bhat
Attorney, Agent, or Firm—Bierman and Muserlian

[57] ABSTRACT

An active principle microencapsulated in an envelope formed by interfacial polymerization of two non-miscible phases A and B, organic phase A comprising at least one water insoluble active principle which do not react with each other, a polyfunctional monomer a and a solvent for the active principle and aqueous phase B comprising a polyfunctional monomber b and a catalyst which allows a progressive diffusion of the active principle and protects the same from the environment.

9 Claims, No Drawings

MICROENCAPSULATION PRODUCT AND PROCESS

OBJECTS OF THE INVENTION

It is an object of the invention to provide novel microcapsulses of an active ingredient and a novel process for their preparation.

This and other objects and advantages of the invention will become obvious from the following detailed description.

THE INVENTION

The novel compositions of the invention are an active principle microencapsulated in an envelope formed by interfacial polymerization of two non-immiscible phases A and B, organic phase A comprising at least one water insoluble active principle which do not react with each other, a polyfunctional monomer and a solvent for the active principle and aqueous phase B comprising a polyfunctional monomer b and a catalyst.

The process of the invention comprises microencapsulating the active principle in an envelope formed by interfacial copolymerization of two immiscible phases A and B, organic phase A comprising at least one water insoluble active principle which do not react with each other, a polyfunctional monomer a and a solvent for the active principle and aqueous phase B comprising a polyfunctional monomer b and a catalyst.

The organic phase A can contain at least one organic solvent for the active principle(s) and in a preferred embodiments, the polyfunctional monomer a acts as the solvent for the active principle(s). The organic phase A may also contain antiultraviolet stabilizers such as benzophenones or benzotriazones or ultraviolet filters or coloring agents such as diazo compounds.

Examples of the polyfunctional monomer a are diesters of phthalic acid such as the methyl, ethyl, butyl or allyl esters used alone or with another solvent such as an hydrocarbon aromatic solvent such as those sold under the mark Solvesso 150 ®.

In the aqueous phase B, the polyfunctional monomer b is preferably an amino plastic resin, preferably a polymethylated formaldehyde melamine resin. It can be tri or hexamethylol. Examples of resins of this type are trimethylated triamino-2,4,6-triazine-1,3,5-cyanouramide melamine resin sold under the mark PROX M 3R ®.

The catalyst in the aqueous phase B is preferably citric acid but other suitable catalysts such as ammonium chloride may be used.

In a preferred embodiment of the invention, organic phase A contains 0.1 to 25% by weight of a water-immiscible active principle, 7.5 to 90% by weight of polyfunctional monomer a and 0 to 25% by weight of solvent and aqueous phase B contains 59 to 94.9% by weight of water, 5 to 40% by weight of polyfunctional monomer b and 0.1 to 1% by weight of catalyst.

The active principles are products used in the field of phytopathology, human or veterinary pharmaceutical products, chemical or microbiological products such as viruses and enzymes, cosmetics, paints and foodstuffs.

Preferably, the products are phytopathological product such as insecticides, acaricides, herbicides, fungicides. Specific preferred insecticides are deltamethrine, tefluthrine, (S)-cyano-3-phenoxy-benzyl (1R,cis,Z)-2,2-dimethyl-3-[3-[2(1,1,1,3,3,3,-)-hexafluoro-]-propenyl]-cyclopropanecarboxylate and pentafluorophenyl methyl (1R,cis)-2,2-dimethyl-3-[2-fluoro-3-methoxy-3-oxo-1-(E)-propenyl]-cyclopropanecarboxylate.

The microencapsulation process of the invention may be effected by dispersing organic phase A into aqueous phase B or by emulsifying the organic phase A into aqueous phase B while progressively adding the polyfunctional monomer b.

The invention brings into play two chemically different polyfunctional monomers a and b, one for example can be trifunctional and the other can be bifunctional. These monomers are then capable of reacting to form covalent bonds between them which allows the formation of a copolymer membrane at the interface of the two immiscible liquid phases, which membrane constitutes the envelope for the microcapsules.

This phase of copolymerization encapsulation is achieved with stirring preferably at a speed of 400 to 4,000 revolutions/minute and at a temperature which can vary between 40° C. and 70° C. In this respect it should be noted that the temperature influences the reaction time and that the speed of stirring influences the diameter of the microcapsules.

The interfacial copolymerization leads to the encapsulation of the organic phase A containing the active principle or principles. After the microencapsulation is finished, a return to ambient temperature takes place, followed by filtering and drying the microcapsules. The drying can be achieved, for example, on a fluidized bed column or on filter paper in a fume, cupboard ventilated with hot air.

The microcapsules of the process of the invention are particularly useful because they allow by the structure and porosity of the membrane a progressive diffusion of active principle (towards the target aimed for). This membrane protects the active principles form certain chemical or physical factors such as humidity, heat, oxidation and excessive volatility.

When they are used in the field of phytopathology, the microcapsules by their controlled release reduce the risks of pollution, toxicity, irritability as well as the dosages and rates of treatment.

The microcapsules are notably characterized in that they are composed of microspheres from 10 to 200 μm in average diameter. The size of the microcapsules can be changed by varying the stirring rate or the thickness of the wall by modifying the initial concentration of the amino-plastic resin.

The microcapsules of the invention are preferably intended to be diluted in a powdered medium, but can also be used in the form of "flowables" or granules which can be used in soil treatments. The invention also has as a subject a phytopathological treatment process characterized in that the microcapsules, as defined above and/or obtained according to the process of the invention are spread on the soil.

In the following examples there are described several preferred embodiments to illustrate the invention. However, it should be understood that the invention is not intended to be limited to the specific embodiments.

EXAMPLE 1

Preparation of microcapsules of pentafluorophenyl methyl (1R,cis) 2,2-dimethyl-3-[2-fluoro-3-methoxy-3-oxo-1-(E)-propenyl]-cyclopropanecarboxylate STEP A: Preparation of the emulsion An organic phase A was emulsified in an aqueous phase B. Phase A contained 0.18 g of pentafluorophenyl methyl (1R,cis)-2,2-dimethyl-3-[2-fluoro-3-methoxy-3-oxo-1-(E)-propenyl]-cyclopropanecarboxylate, 18.11 g of methyl phthalate and 1.71 g of Solvesso 150 ® solvent for a total weight of 20 g.

Phase B contained 80 g of distilled water and 0.5 g of citric acid. To facilitate the emulsion, the mixture with a pH of 6.4 was stirred at room temperature for a uniform dispersion.

STEP B: Microencapsulation

The reaction was started by adding 1.5 g of PROX M 3R ® resin at 50% W/W in water and the mixture was heated to a temperaturepg 65° C. for 2 and a half hours during which the pH went from 6.4 to 4.8 and the polymerization reaction started. The medium was fed progressively with resin at 50% W/W in water, by adding 12.5 g of PROX M 3R ® until the reaction was exhausted. After the microencapsulation was finished and the temperature had return to ambient at the end of an hour, the microcapsules obtained were filtered and dried. The microcapsules had an average diameter of 100μ.

Analysis: HPLC: 0.7% W/W

EXAMPLE 2

The same preparation process for the microcapsules was followed but the initial quantities of the components of organic phase A were 1.80 of pentafluorophenyl methyl (1R,cis) 2,2-dimethyl-3-[2-fluoro-3-methoxy-3-oxo-1-(E)-propenyl-cyclopropanecarboxylate, 16.49 g of methyl phthalate and 1.71 g of Solvesso 150 ® solvent for a total weight of 20 g. The microcapsules had an average diameter of 100μ.

Analysis: HPLC: 7% W/W

EXAMPLE 3

The same preparation process for the microcapsules were followed but the initial components of organic phase A were 3.43 g of pentafluorophenyl methyl (1R,cis)-2,2-dimethyl-3-[2-fluoro-3-methoxy-3-oxo-1-(E)-propenyl]-cyclopropanecarboxylate, 14.86 g of methyl phthalate and 1.71 g of Solvesso 150 ® solvent. The microcapsules had an average diameter of 100μ.

Analysis: HPLC: 13.40% W/W.

Various modifications of the products and processes of the invention may be made without departing from the spirit or scope thereof and it should be understood that the invention is intended to be limited only as defined in the appended claims.

What is claimed is:

1. Active principle microencapsulated in an envelope formed by interfacial polymerization of two non-miscible phases A and B, organic phase A comprising at least one water insoluble active principle which do not react with each other, a polyfunctional monomer a which is a diester of phthalic acid and a solvent for the active principle and aqueous phase B comprising a polyfunctional monomer b which is an amino plastic resin and a catalyst.

2. The active principle of claim 1 wherein phase A is dispersed in phase B for the polymerization.

3. The active principle of claim 1 wherein phase A is emulsified in phase B and monomer b is progressively added.

4. The active principle of claim 1 wherein monomer b is a polymethylated triamino-1,4,6-triazine-1,3,5-cyanoamide melamine resin.

5. The active principle of claim 1 wherein organic phase A is comprised of 0.1 to 25% by weight of water-insoluble active principle, 7.5 to 90% by weight of polyfunctional monomer a and 0 to 25% by weight of organic solvent.

6. The active principle of claim 1 wherein aqueous phase B comprises 59 to 94.9% by weight of water, 5 to 40% by weight of polyfunctional monomer b and 0.1 to 1% by weight of catalyst.

7. The active principle of claim 1 which is a pyrethrinoid.

8. The active principle of claim 1 wherein the pyrethrinoid is selected from the group consisting of deltamethrine, tefluthrine, (S) -cyano-3-phenoxy-benzyl (1R,cis,Z) 2,2-dimethyl-3-[3-[2-(1,1,1,3,3,3)-hexafluoro]-propoxy-3-oxo-1-propenyl]-cyclopropanecarboxylate and pentafluorophenyl methyl (1R,cis) 2,2-dimethyl -3-[2-fluoro-3-methoxy-3-oxo-1-(E)-propenyl]-cyclopropanecarboxylate.

9. A process for the microencapsulation of an active principle of claim 1 comprising microencapsulating the active principle in an envelope formed by interfacial copolymerization of two immiscible phases A and B, organic phase A comprising at least one water insoluble active principle which do not react with each other, a polyfunctional monomer a and a solvent for the active principle and aqueous phase B comprising a polyfunctional monomer b and a catalyst.

* * * * *